United States Patent
Kolano et al.

(10) Patent No.: US 9,056,828 B2
(45) Date of Patent: Jun. 16, 2015

(54) ALKOXYLATION METHOD OF FATTY ACID ALKYL ESTERS

(75) Inventors: Christoph Kolano, Zurich (CH); Lothar Möhle, Wettswil a. A. (CH); Rudolf Richner, Waltenschwil (CH)

(73) Assignee: Kolb Distribution Ltd., Hedingen (CH)

( * ) Notice: Subject to any disclaimer, the term of this patent is extended or adjusted under 35 U.S.C. 154(b) by 123 days.

(21) Appl. No.: 13/818,265

(22) PCT Filed: Aug. 11, 2011

(86) PCT No.: PCT/EP2011/063830
§ 371 (c)(1), (2), (4) Date: Feb. 21, 2013

(87) PCT Pub. No.: WO2012/028435
PCT Pub. Date: Mar. 8, 2012

(65) Prior Publication Data
US 2013/0150601 A1 Jun. 13, 2013

(30) Foreign Application Priority Data
Sep. 2, 2010 (EP) .................................... 10175014

(51) Int. Cl.
| | |
|---|---|
| C07C 67/26 | (2006.01) |
| C07C 67/29 | (2006.01) |
| C11C 3/00 | (2006.01) |
| C07B 41/04 | (2006.01) |
| C08G 65/332 | (2006.01) |

(52) U.S. Cl.
CPC ............... *C07C 67/29* (2013.01); *C07C 67/26* (2013.01); *C11C 3/003* (2013.01); *C07B 41/04* (2013.01); *C08G 65/3322* (2013.01)

(58) Field of Classification Search
None
See application file for complete search history.

(56) References Cited

U.S. PATENT DOCUMENTS

| | | | |
|---|---|---|---|
| 4,115,415 A | 9/1978 | Yoshihara et al. | |
| 5,220,046 A * | 6/1993 | Leach et al. | ............. 554/149 |
| 6,008,392 A | 12/1999 | Behler et al. | |
| 6,184,400 B1 | 2/2001 | Hama et al. | |

FOREIGN PATENT DOCUMENTS

| | | |
|---|---|---|
| DE | 196 11 999 C1 | 7/1997 |
| EP | 2 181 763 A1 | 5/2010 |
| JP | 5077312 A | 6/1975 |
| WO | 02/38269 A1 | 5/2002 |
| WO | 2006/025898 A1 | 3/2006 |

* cited by examiner

*Primary Examiner* — Yate K Cutliff
(74) *Attorney, Agent, or Firm* — Sughrue Mion, PLLC

(57) ABSTRACT

The present invention is directed towards a method of preparing alkoxylated fatty acid alkyl estersin a one-pot alkoxylation reaction in the presence of a catalyst which is an alkaline earth metal oxide/mineral acid combination, preferably a barium oxide/sulfuric acid combination, or a Lewis acid, preferably $SnCl_4$, comprising the steps of: a) providing a fatty acid alkyl ester, b) adding a catalyst to said fatty acid alkyl ester to obtain a first mixture, wherein said catalyst is an alkaline earth metal oxide/mineral acid combination or a Lewis acid, c) adding one or more alkylene oxides to said first mixture to obtain a second mixture and (d) isolating the alkoxylated fatty acid alkyl ester.

24 Claims, 3 Drawing Sheets

ALKOXYLATION METHOD OF FATTY ACID ALKYL ESTERS

CROSS REFERENCE TO RELATED APPLICATIONS

This application is a National Stage of International Application No. PCT/EP2011/063830 filed Aug. 11, 2011, claiming priority based on European Patent Application No. 10 175 014.9 filed Sep. 2, 2010, the contents of all of which are incorporated herein by reference in their entirety.

FIELD OF THE INVENTION

The present invention is directed towards a method of preparing alkoxylated fatty acid alkyl esters in a one-pot alkoxylation reaction in the presence of a catalyst which is an alkaline earth metal oxide/mineral acid combination or a Lewis acid.

BACKGROUND

Alkoxylated fatty acid alkyl esters belong to the class of non-ionic surfactants and are widely used for various applications.

While the well known addition of alkylene oxides onto fatty acids, i.e. compounds containing acidic hydrogen atoms, can be carried out in the presence of various, generally alkaline catalysts, the insertion of alkylene oxides into the ester bond of a fatty acid alkyl ester is far more difficult and can only be achieved using special catalysts.

There have been many attempts to obtain catalysts for alkoxylation of fatty acid alkyl esters that are both efficient as well as easy to prepare and use. Typically these compounds comprise alkaline earth metal compounds, in particular calcium and magnesium, in admixture with various cocatalysts. Representative examples include e.g. mixtures of at least two alkaline earth compounds and one or more additional materials selected from a carboxylic acid; a polyalkylene glycol, an $C_1$-$C_{10}$ alkyl-capped polyalkylene glycol and mixtures thereof together with at least one acid (WO 2006/025898). Other catalysts are based on mixtures of one or more alkaline earth metal salts of carboxylic and/or hydroxycarboxylic acids, an oxyacid, an alcohol and/or an ester, and a peroxy acid and/or a salt thereof (EP-A-2181763) or calcium salts of low molecular carboxylic and/or hydroxycarboxylic acids and/or hydrates of the former, in combination with a strong oxyacid, and an alcohol and/or an ester (WO 02/38269).

However, presently known methods of alkoxylating of fatty acid alkyl esters are still suffering from several disadvantages, in particular the need for external preparation of the catalyst (i.e. isolation of intermediates, etc.), the lack of a peaked homologue distribution, as well as unfavourable reaction conditions (e.g. high temperatures), etc. Thus, there is still a need for alkoxylation methods of fatty acid alkyl esters with both suitable and convenient reaction conditions as well as excellent reaction outcome (suitable for industrial scale).

Applicants have now found that a catalyst system based on either an alkaline earth metal oxide/mineral acid combination, in particular $BaO/H_2SO_4$, or a Lewis acid, in particular $SuCl_4$, is able to overcome the problems associated with the prior art methods. In particular it was shown that the alkoxylation reaction of fatty acid alkyl esters results in alkoxylated products having a narrow oligomer distribution when an alkaline earth metal oxide/mineral acid combination, in particular $BaO/H_2SO_4$ combination, or to Lewis acid, in particular $SnCl_4$, is used as a catalyst. Furthermore these methods can be performed in a one-pot reaction therefore eliminating the step of isolating any intermediate compounds, such as the external preparation of the catalyst and subsequent transfer into another reactor for the alkoxylation reaction according to the prior art.

SUMMARY OF THE INVENTION

Accordingly, it is one object of this invention to provide a novel method of preparing alkoxylated fatty acid alkyl ester a one-pot alkoxylation reaction in the presence of a catalyst which is an alkaline earth metal oxide/mineral acid combination or a Lewis acid.

More specifically, the invention is directed towards a method for preparing an alkoxylated fatty acid alkyl ester in a one-pot reaction comprising the steps of: (a) providing a fatty acid alkyl ester, (b) adding a catalyst to said fatty acid alkyl ester to obtain a first mixture, wherein said catalyst is an alkaline earth metal oxide/mineral acid combination or a Lewis acid, (c) adding one or more alkylene oxides to said first mixture to obtain a second mixture and (d) isolating the alkoxylated fatty acid alkyl ester.

In one embodiment, the alkoxylate fatty acid alkyl ester has the formula $R_1$—COO—$[(CH_2$—$CHR_3$—$O)_x$—$(CH_2$—$CHR_4$—$O)_y]_z$—$R_2$.
wherein $R_1$ and $R_2$ are independently each other a linear or branched, saturated or unsaturated, aliphatic or aromatic hydrocarbon radical having from 1 to 30 carbon atoms,
$R_3$ and $R_4$ are independently of each other H, (C1-C10)alkyl, preferably H, methyl or ethyl,
x, y and z are independently of each other an integer having average value from 1 to 100, with the proviso that $(x+y) \cdot z \leq 100$.

In other embodiments, the alkaline earth metal oxide is an oxide of Group II elements, preferably barium oxide. The mineral acid is selected from sulfuric acid, hydrochloric acid, perchloric acid, nitric acid, phosphoric acid, preferably sulfuric acid.

In yet other embodiments the Lewis acid is a tin halide, preferably fuming $SnCl_4$.

According to a preferred process of the invention, the catalyst is a combination of barium oxide and sulfuric acid in a ratio of 1.5-2.5 to 0.5-1.5, preferably about 2:1.

These and other objects which will become apparent from the following specification.

DETAILED DESCRIPTION

Figure 1A:
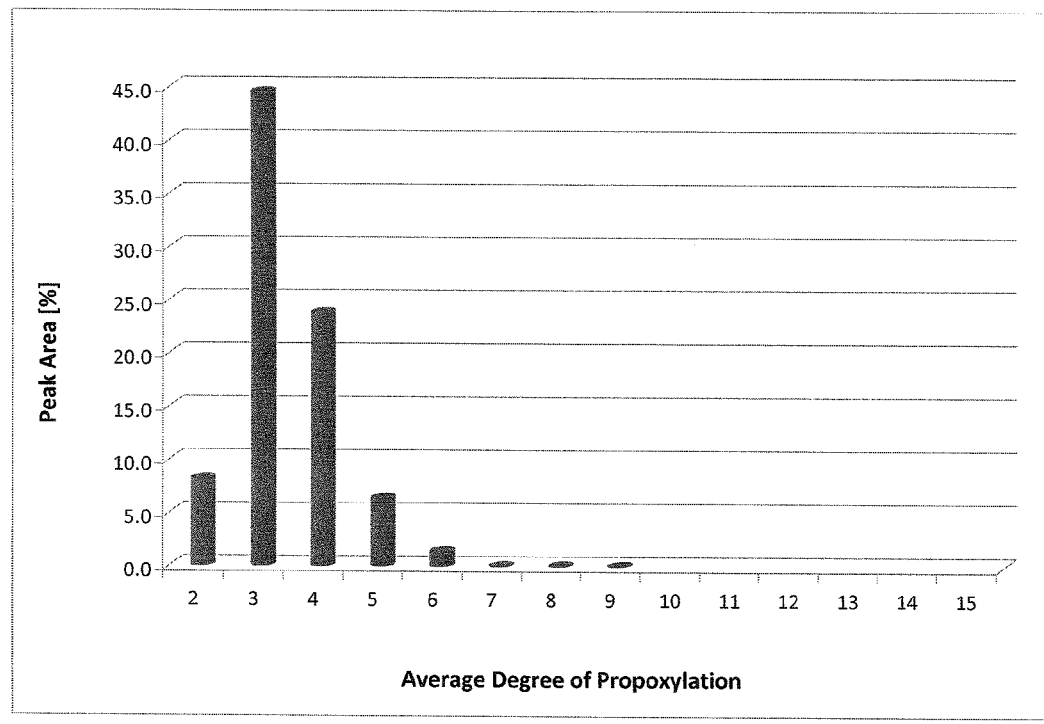
FIG. 1(a)-(d): Homologue distribution of various alkoxylated Palmere M1218 PK: (a) 4.3 M PO, (b) 10 M EO, (c) 7 M EO in comparison with a prior art catalyst system (filled columns: catalyst system of the invention, striped columns: prior art catalyst system (methylester ethoxylate isolated from liquid laundry detergent), (d) 3 M EQ.
Figure 1B:
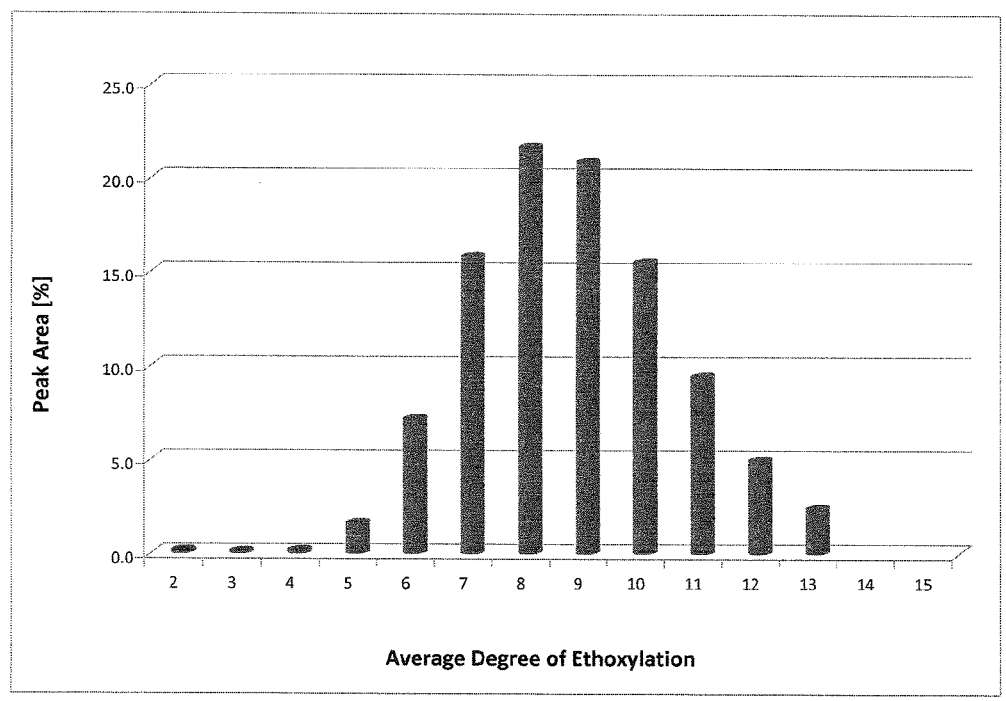
Figure 1C:
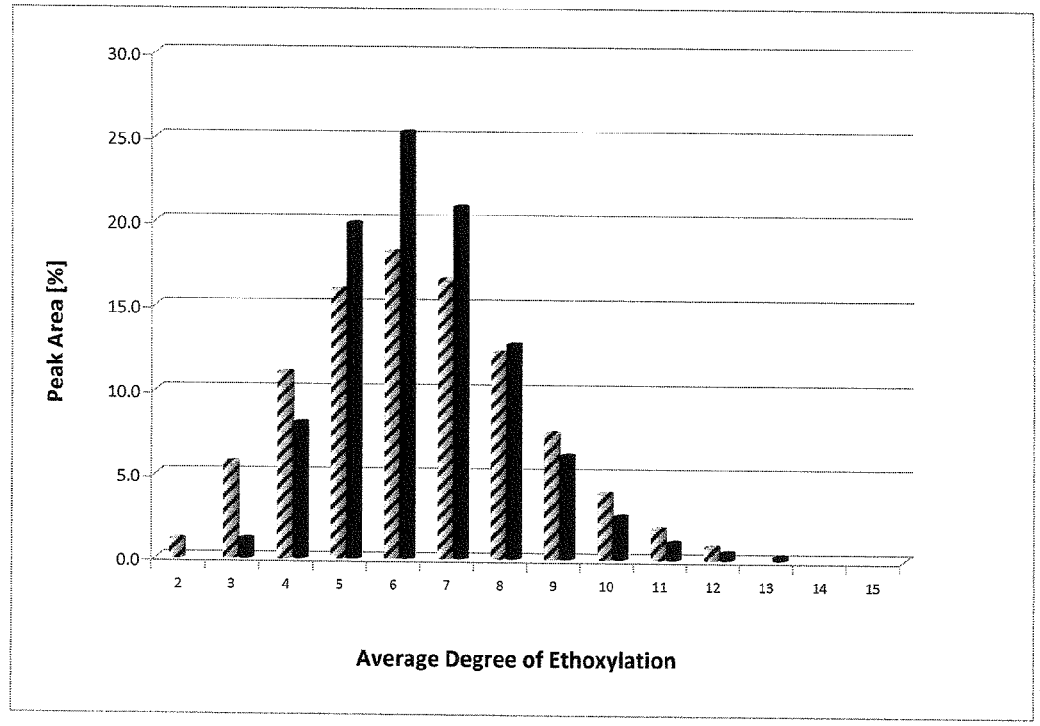
Figure 1D:
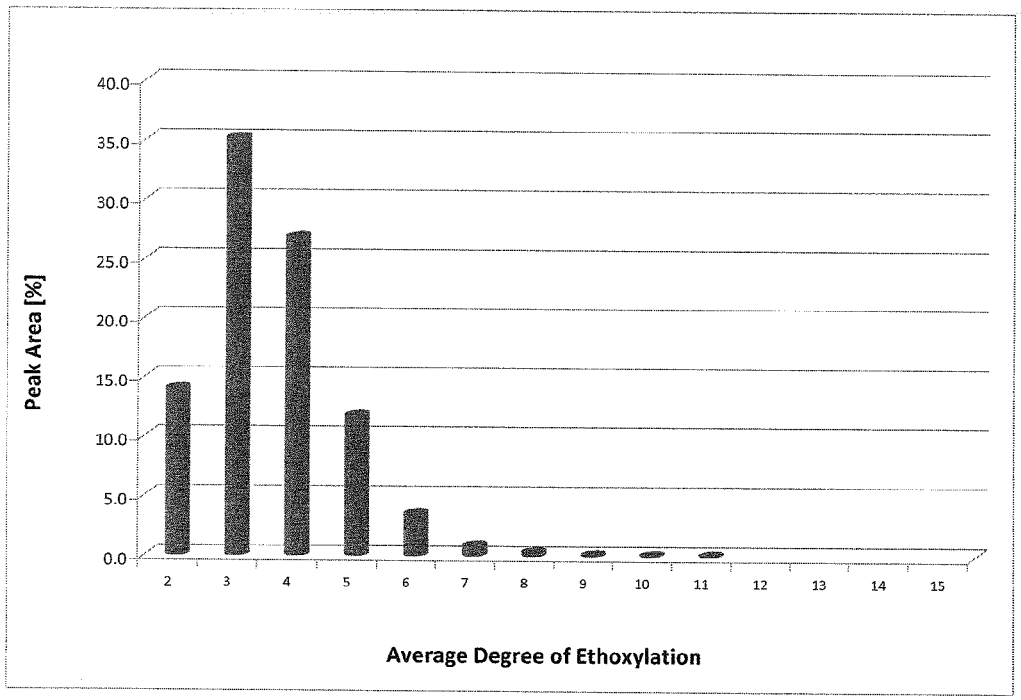
Figure 2:
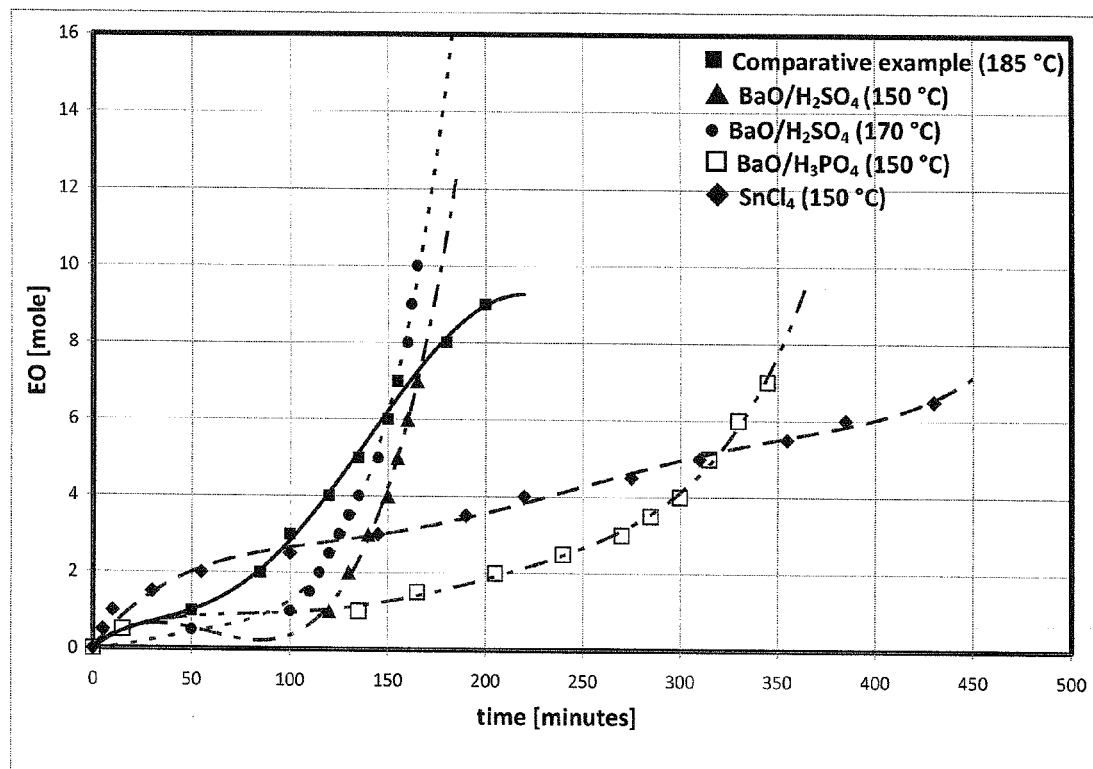
FIG. 2: Kinetic data fix ethoxylation of Palmere M1218 PK: Degree of ethoxylation vs. reaction time with different catalyst systems of the present invention in comparison to the catalyst system of the prior art. The filled triangle indicates ethoxylation using $BaO/H_2SO_4$ (at, 150° C.), the filled circle shows ethoxylation using $BaO/H_2SO_4$ (at 170° C.), the empty square indicates ethoxylation using $BaO/H_3PO_4$ (at 150° C.) and the filled diamond shows fuming $SnCl_4$ (at 150° C.). The lifted square indicates a prior art catalyst system (GEO-2 catalyst of WO 2006/025898 Huntsman Petrochemical Corp., p. 11).

Provided herein are methods for preparing alkoxylated fatty acid alkyl esters in a one-pot alkoxylation reaction (also called methods of the invention) in the presence of a catalyst which is an alkaline earth metal oxide/mineral acid combination or a Lewis acid.

More specifically, the methods of the invention comprise the step of reacting a fatty acid alkyl ester with one or more alkylene oxides in the presence of a catalyst, wherein the catalyst is either an alkaline earth metal oxide/mineral acid combination or a Lewis acid. Thus, the methods of the invention comprise the steps of: a) providing a fatty acid alkyl ester, b) adding a catalyst to said fatty acid alkyl ester to obtain a first mixture, wherein said catalyst is an alkaline earth metal oxide/mineral acid combination or a Lewis acid, c) adding one or more alkylene oxides to said first mixture to obtain a second mixture and (d) isolating the alkoxylated fatty acid alkyl ester from said second mixture.

The term "one-pot" reaction as used herein refers to a reaction composing series of steps that may be performed in a single reaction vessel. One-pot procedures may eliminate the need for isolation (e.g., purification) of intermediates while reducing the production of waste materials (e.g., solvents, impurities, side reaction products). Other advantages include ease of handling and typically reduction of overall reaction time.

The term "isolating" is used to indicate separation or collection or recovery of the obtained alkoxylated fatty acid alkyl ester according to standard procedures, preferably by filtration.

The fatty acid alkyl esters that are used in the present methods as starting material are not particularly limited and may be any one of animal based oils and fats derived from beef tallow, fish oil, lanolin, etc.; plant based oils and fats derived from coconut oil, palmoil, soybeanoil, etc.; synthetic fatty acid alkyl esters derived from α-olefins by means of using an oxo-synthesis method.

Typically, the fatty acid alkyl esters include compounds of the formula $R_1$—COO—$R_2$, wherein $R_1$ and $R_2$ are independently of each other a linear or branched, saturated or unsaturated, aliphatic or aromatic hydrocarbon radical haying from 1 to 30 carbon atoms.

The term "unsaturated" as used herein refers to "the state in which not all of the available valence bonds along an alkyl chain are satisfied" (Hawley's Condensed Chemical Dictionary, 1151, 14th Edition, 2002, by John Wiley & E Sons, Inc.). More specifically, the term "unsaturated" in reference to a fatty acid alkyl ester refers to the presence of at least one double bond, preferably 1 to 3 double bonds in the hydrocarbon chain $R_1$. The term "substituted" in reference to a fatty acid alkyl ester refers to substitution of the hydrocarbon chain $R_1$ by groups selected from hydroxy, oxo, carboxyl, amino, C1-C6-alkyl, C1-C6-alkenyl and C1-C6-alkoxyhydroxyl, and the like In a specific embodiment, $R_1$ is a linear or branched, saturated unsaturated, aliphatic or aromatic hydrocarbon radical having from 6 to 22 carbon atoms.

In another specific embodiment, $R_2$ is a linear or branched, saturated or unsaturated or aromatic hydrocarbon radical having from 1 to 22 carbon atoms, preferably 1 to 18 carbon atoms, preferably 1 to 12 carbon atoms, more preferably 1 to 8 carbon atoms, more preferably methyl, ethyl, propyl, isopropyl butyl, most preferably methyl.

Typical examples of fatty acid alkyl esters include, but are not limited to, methyl, ethyl, propyl, butyl and/or stearyl esters of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils or in the reduction of aldehydes from Roelen's oxosynthesis. Cocofatty acid and/or tallow fatty acid methyl esters are preferably used as starting materials.

These fatty acid alkyl esters may be used singly or as mixtures of two or more of them.

In a typical method of the invention a fatty acid alkyl ester of formula $R_1$—COO—$R_2$ is reacted with one or more alkylene oxide in the presence of a catalyst which is an alkaline earth metal oxide/mineral acid combination or a Lewis acid to give an alkoxylated fatty acid alkyl ester.

As used herein the term "alkylene oxide" refers to ethylene oxide, propylene oxide, 1,2- or 2,3-butylene oxide, pentylene oxide, hexylene oxide, heptylene oxide, octylene oxide, nonylene oxide, decylene oxide and cyclohexylene oxide; aromatic epoxides such as styrene oxide and 2-methylstyrene oxide; and hydroxy- and halogen-substituted alkylene oxides such as glycidol, epichlorhydrin and epibromhydrin, and mixtures thereof. In specific embodiments, the one or more alkylene oxide includes one single alkylene oxide or a mixture of 2 alkylene oxides as defined above. Preferred alkylene oxides include one or more 1,2-alkylene oxides, most preferably ethylene oxide, propylene oxide or butylene oxide and mixtures thereof.

The term "alkoxylated fatty acid alkyl ester" as used herein refers to a fatty acid alkyl ester as defined hereinabove, that has been subjected to the alkoxylation methods of the present invention. Typically an alkoxylated fatty acid alkyl ester includes compounds of the formula

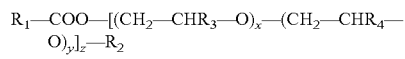

$R_1$—COO—[(CH$_2$—CHR$_3$—O)$_x$—(CH$_2$—CHR$_4$—O)$_y$]$_z$—$R_2$ wherein $R_1$ and $R_2$ are independently of each other a linear or branched, saturated or unsaturated, aliphatic or aromatic, hydrocarbon radical having from 1 to 30 carbon atoms, $R_3$ and $R_4$ are independently of each other H, (C1-C10)alkyl, preferably H, methyl or ethyl, x, y and z are independently of each other an integer having an average value from 1 to 100, with the proviso that (x+y)·z≤100.

In one embodiment only one type of alkylene oxide is incorporated. Thus, one of x and y is 0, the other is a value from 1 to 100, and z is 1.

In another embodiment two different alkylene oxides are incorporated in random fashion, alternating fashion or in block-type fashion. Thus, for example x and y may be both 1 and 2 may range from 1 to 50 (alternating fashion), or x and y may be greater than 1 (block-type fashion. Typical combination of alkylene oxide units may be ethylene oxide and propylene oxide.

In other embodiments, $R_1$ is a linear or branched, saturated or unsaturated, aliphatic or aromatic hydrocarbon radical having from 6 to 22 carbon atoms.

In yet other embodiments, $R_2$ is a linear or branched, saturated or unsaturated, aliphatic or aromatic hydrocarbon radical having from 1 to 22 carbon atoms, preferably 1 to 18 carbon atoms, preferably 1 to 12 carbon atoms, more preferably 1 to 8 carbon atoms, more preferably methyl, ethyl, propyl, isopropyl butyl, most preferably methyl.

In another specific embodiment x has an average value of preferably 1 to 40, more preferably 3 to 20.

In some embodiments the alkoxylated fatty acid alkyl ester is saturated, in other embodiments the fatty acid alkyl ester has from one to three double bonds.

It is understood, that all specific embodiments of the fatty acid alkyl esters used as starting materials disclosed hereinabove also apply to the alkoxylated fatty acid alkyl esters.

In one preferred embodiment, alkoxylated fatty acid alkyl esters are compounds of the Formula

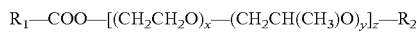

$$R_1—COO—[(CH_2CH_2O)_x—(CH_2CH(CH_3)O)_y]_z—R_2$$

wherein $R_1$ is a linear or branched, saturated or unsaturated, aliphatic or aromatic hydrocarbon radical having from 1 to 30 carbon atoms, preferably 6 to 22 carbon atoms.

$R_2$ is a linear or branched, saturated or unsaturated, aliphatic or aromatic hydrocarbon radical having from 1 to 22 carbon atoms, preferably 1 to 12 carbon atoms, more preferably 1 to 8 carbon atoms, more preferably methyl, ethyl, propyl, butyl, most preferably methyl.

x, y and z are independently of each other an integer having an average value from 1 to 100, with the proviso that $(x+y)\cdot z \leq 100$.

In another preferred embodiment, alkoxylated fatty acid alkyl esters are compounds of the Formula

$$R_1—COO—(CH_2CHR_3O)_x—R_2$$

wherein $R_1$ is a linear or branched, saturated or unsaturated, aliphatic or aromatic hydrocarbon radical having from 1 to 30 carbon atoms, preferably 6 to 22 carbon atoms.

$R_2$ is a linear or branched, saturated or unsaturated, aliphatic or aromatic hydrocarbon radical having from 1 to 22 carbon atoms, preferably 1 to 12 carbon atoms, more preferably 1 to 8 carbon atoms, more preferably methyl, ethyl, propyl, butyl, most preferably methyl.

$R_3$ is H or (C1-C10)alkyl, preferably H, methyl or ethyl x is an integer having an average value from 1 to 100.

Preferred alkoxylated fatty acid alkyl esters are alkoxylated fatty acid methyl esters, more preferably ethoxylated and/or propoxylated fatty acid methyl esters of formulas $R_1—COO—[CH_2CH_2)O]_x—CH_3$ or $R_1—COO—[CH_2CH(CH_3)O]_x—CH_3$ wherein $R_1$ is a substituted or unsubstituted, linear or branched, saturated or unsaturated, aliphatic or aromatic hydrocarbon radical having from 1 to 30 carbon atoms preferably 6 to 22 carbon atoms, and x is an integer having an average value from 1 to 100, preferably 1 to 40, more preferably 3 to 20; or of formula $R_1—COO—[(CH_2CH_2O)_x—(CH_2CH(CH_3)O)_y]_z—CH$ wherein $R_1$ is a substituted or unsubstituted, linear or branched, saturated or unsaturated, aliphatic or aromatic hydrocarbon radical having from 1 to 30 carbon atoms, preferably 6 to 22 carbon atoms, and x, y and z are independently of each other an integer having an average value from 1 to 100, with the proviso that $(x+y)\cdot z\leq 100$, preferably a value from 1 to 40, with the proviso that $(x+y)\cdot z\leq 100$.

The ratio of fatty acid alkyl ester to one or more alkylene oxide depends on the nature of the fatty acid alkyl ester to be alkoxylated and the desired characteristics of the alkoxylated product (which depend on its intended use). Typically the ratio of fatty acid alkyl ester to one or more alkylene oxide may range from about 1 to 100, preferably 1 to 25 (moles of alkylene oxide per mole of alkyl ester).

As used herein the term "alkaline earth metal oxide" refers to an oxide of Group II elements of the Periodic Table, e.g., calcium, strontium, barium, preferably barium oxide.

The alkaline earth metal oxide may be used in an amount of less than 5 wt %, preferably less than 3 wt %, more preferably less than 1.5 wt %. In preferred embodiments the alkaline earth metal oxide may be used from 0.1 to 5 wt %, more preferably from 0.5 to 3 wt %, most preferably from 0.5 to 1.5 wt %, based on the amount of fatty acid alkyl ester of choice.

As used herein the term "mineral acid" refers to sulfuric acid, hydrochloric acid, perchloric, acid, nitric acid, phosphoric acid, and the like, preferably sulfuric acid. Sulfuric acid includes oleum or fuming sulfuric acid, concentrated sulfuric acid which contains at least 95% by weight of $H_2SO_4$ as well as less concentrated forms of sulfuric acid, but preferably containing more than 60% sulfuric acid The mineral acid, which is used as a cocatalyst in combination with an alkaline earth metal oxide, may be used in an amount of less than 5 wt %, preferably less than 3 wt %, more preferably less than 2 wt %. In preferred embodiments the mineral acid may be used from 0.01 to 5 wt %, more preferably from 0.01 to 3 wt %, most preferably from 0.1 to 2 wt %, based on the amount of fatty acid alkyl ester of choice.

If an alkaline earth metal oxide/mineral acid combination is used as a catalyst, the preferred ratio of alkaline earth metal oxide to mineral acid as defined above (preferably sulfuric acid) may be in the range of from 15-2.5 to 0.5-1.5, preferably about 2:1.

As used herein the terra "Lewis acid" refers to a halide, particularly a chloride, of the elements of the 3rd and 4th main group and 4th and 8th secondary group of the periodic system of elements, typically boron trifluoride, aluminium trichloride, germanium tetrachloride, tin dichloride, tin tetrachloride, titanium tetrachloride. Tin halides, particularly chlorides of tin in its oxidation stage+IV (i.e. tin tetrachloride), are preferably used.

The Lewis acid may be used in an amount of 0.2-1.5 wt % and preferably in an amount of 0.5-1.0 wt % based on the amount of fatty acid ester of choice.

Typically, the methods of the invention further comprise, the step of drying the first mixture of step (b) in vacuo at a temperature of from 40° to 140° C., preferably 80° to 140° C., before subjecting it to step (c). The one or more alkylene oxides are preferably added gradually to the first mixture to control the exothermicity of the reaction. Preferably, step (c) is conducted at a pressure of 0.1 to 10 bar, more preferably 0.1 to 2.0 bar. Preferably, step (c) is carried out at a temperature not lower than the melting point of the fatty acid alkyl ester, and preferably ranges from the melting point of the fatty acid alkyl ester to a temperature of 200° C. more preferably from 40° C. to 200° C., most preferably 160° to 200° C.

In other embodiments, the alkaline earth metal oxide and the mineral acid are added simultaneously or sequentially, without external premixing of the catalyst.

In other embodiments, the second mixture obtained in step (c) of the methods of the invention is acidified for neutralization prior to step (d). The obtained alkoxylated fatty acid alkyl ester is preferably isolated by filtration.

Thus in accordance with a preferred embodiment of the invention, the methods of the invention comprise the steps of i) providing a fatty acid alkyl ester, ii) adding a catalyst to said fatty acid alkyl ester to obtain a first mixture, wherein said catalyst is an alkaline earth metal oxide/mineral acid combination or a Lewis acid, iii) drying the first mixture obtained in step (ii) in vacuo at a temperature of from 40° to 140° C. Preferably 80° to 140° C. (iv) adding one or more alkylene oxide to the dried first mixture at a pressure of 0.1 to 10 bar, more preferably 0.1 to 2.0 bar, and at a temperature of from 40° C. to 200° C., more preferably 160° to 200° C. to obtain a second mixture, (v) acidifying the second mixture (for neutralization) and (vi) isolating the alkoxylated fatty acid alkyl ester from the acidified second mixture.

According to a preferred process of the invention, the catalyst is a combination of barium oxide and sulfuric acid in a ratio of 1.5-2.5 to 0.5-1.5, preferably about 2:1.

According to another preferred process of the invention, the catalyst is (fuming) SnCl$_4$.

The alkoxylation methods of the present invention are not particularly limited to one specific type of reaction vessel, but may conveniently be carried out in a glass autoclave with thermo-jacket (attached to a circulation thermostat) preferably equipped with art overhead stirrer and thermocouple. Therein the fatty acid alkyl ester of choice is placed. The reaction vessel may be evacuated and purged with an inert gas, such as nitrogen, once or more times.

Subsequently, an anhydrous alkylene earth metal oxide, preferably barium oxide, and a mineral acid, preferably sulfuric acid, are added sequentially (or batchwise) at ambient temperature to the ester while stirring. The term "ambient temperature", for the purposes of the present method, refers to a temperature between 15° C. and 30° C., preferably 20° C. to 25° C. The circulation thermostat is set to a temperature at which the fatty acid alkyl ester shows flowability, which depends on the choice of ester or mixture of esters. Stirring is continued for up to 10 minutes, preferably 1 to 10 minutes.

The resulting mixture is subsequently vacuum dried at about 100° C. to remove residual moisture. Then, the reaction temperature within the reactor is elevated to a predetermined temperature as defined above. Subsequently, at least one alkylene oxide, preferably ethylene oxide, propylene oxide or a mixture thereof, is introduced into the reactor, and brought into contact with the fatty acid alkyl ester mixture. Typically the alkylene oxide(s) are fed to the reactor using a pressure feed back loop to control feed rate to maintain the (autogeneously generated) pressure in the reactor (which rises due to the exothermic reaction) below 10 bar, i.e. between 0.1 to 10 bar, more preferably between 0.1 and 2 bar throughout the process.

Completion of the reaction is indicated by the consumption of the alkylene oxide(s). Once the reaction is completed, the reactor is cooled and vented. The obtained crude product is neutralized with an acid, typically acetic acid, hydrochloric acid, lactic acid, phosphoric acid, and the like, and the crude product is filtered to give pure alkoxylated fatty acid alkyl ester.

The same procedure was used in case of fuming Sn(+IV)Cl$_4$ as the catalyst, with the exception that no neutralization step was required.

The followings examples illustrate the present invention without limiting the invention in any way.

Example 1

Preparation of Narrow Range Fatty Acid Methyl Ester Ethoxylate

A 2.5 L glass autoclave with thermo-jacket (attached to a circulation thermostat) equipped with an overhead stirrer, and thermocouple is charged with 362 g Palmere M1218 PK (KLK Oleomas, Malaysia). Subsequently, 5.25 g of anhydrous barium oxide and 2.3 g of sulfuric acid (76%) is added to the ester. The mixture was first vacuum dried at about 100° C. for about one hour to remove residual moisture. The reactor was heated to about 160° C., and ethylene oxide (MW 44.06 g/mol) was added to an initial pressure of 0.5 bar. After an induction period, a small exothermic reaction is observed on which the addition of ethylene oxide is continued at a pressure of 2 bar, until 462 g of ethylene oxide in total have been consumed. The reaction temperature at this point is 180-190° C. After the reaction a cook-down time of one hour is applied to the product. The product is neutralized with approximately 5 g acetic acid (80%). The yield after filtration is 90% of a 7 mole ethoxylate.

Using similar technique, 3.0, 10.0, and 15.0 mole ethoxy of Palmere M1218 PK were prepared.

Example 2

Preparation of Narrow Range Fatty Acid Methyl Ester Propoxylate

A 2.5 L glass autoclave with thermo-jacket (attached to a circulation thermostat) equipped with an overhead stirrer, and thermocouple is charged with 241 g Palmere M1218 PK (KLK Oleomas, Malaysia). Subsequently, 3.5 g of anhydrous barium oxide and 1.53 g of sulfuric acid (76%) is added to the ester. The mixture was first vacuum dried at about 100° C. for about one hour to remove residual moisture. The reactor was heated to about 160° C., and propylene oxide (MW 58.08 g/mol) was added to an initial pressure of 0.5 bar. After an induction period a small exothermic reaction is observed on which the addition of propylene oxide is continued at a pressure of 2 bar, until 252 g of propylene oxide in total have been consumed. The reaction temperature at this point is 180-190° C. After the reaction a cook-down time of one hour is applied to the product. The product is neutralized with approximately 1 g acetic acid (80%). The yield after filtration is 90% of a 4.3 mole propoxylate.

Using similar technique, 3.0, 5.0, and 7.0 mole propoxylates Palmere M1218 PK were prepared.

Example 3

Preparation of Narrow Range Fatty Acid Methyl Ester Ethoxylate

A 2.5 L glass autoclave with thermo-jacket (attached to a circulation thermostat) equipped with an overhead stirrer, and thermocouple is charged with 362 g Palmere M1218 PK (KLK Oleomas, Malaysia). Subsequently, 5.25 g of fuming stannous (IV) chloride is added to the ester. The mixture was first vacuum dried at about 100° C. for about one hour to remove residual moisture. The reactor was heated to about 160° C., and ethylene oxide (MW 44.06 g/mol) was added to an initial pressure of 0.5 bar. After an induction period a small exothermic reaction is observed on which the addition of ethylene oxide is continued at a pressure of 2 bar, until 429 g of ethylene oxide in total have been consumed. The reaction temperature at this point is 150-160° C. After the reaction a cook-down time of one hour is applied to the product. The product did not require neutralization. The yield after filtration is 90% of a 6.5 mole ethoxylate

The invention claimed is:

1. A method for preparing an alkoxylated fatty acid alkyl ester in a one-pot reaction comprising the steps of:
    (a) providing a fatty acid alkyl ester,
    (b) adding a catalyst to said fatty acid alkyl ester to obtain a first mixture, wherein said catalyst is an alkaline earth metal oxide/mineral acid combination or a Lewis acid that is a halide of the elements of the 3$^{rd}$ an 4$^{th}$ main group and 4$^{th}$ and 8$^{th}$ secondary group of the periodic system of elements,
    (c) adding one or more alkylene oxides to said first mixture to obtain a second mixture and
    (d) isolating the alkoxylated fatty acid alkyl ester.

2. A method according to claim 1, wherein the alkoxylated fatty acid alkyl ester has the formula:

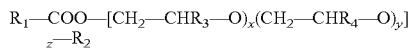

wherein
R$_1$ and R$_2$ are independently of each other a linear or branched, saturated or unsaturated, aliphatic or aromatic hydrocarbon radical having from 1 to 30 carbon atoms,
R$_3$ and R$_4$ are independently of each other H, (C1-C10)-alkyl,
x, y and z are independently of each other an integer having an average value from 1 to 100,
with the proviso that (x+y)·z≤100.

3. A method according to claim 1, wherein the alkaline earth metal oxide and the mineral acid are added simultaneously or sequentially.

4. A method according to claim 3, wherein the alkaline earth metal oxide is an oxide of Group II elements.

5. A method according to claim 4, wherein the alkaline earth metal oxide is at a concentration of less than 5 wt %.

6. A method according to claim 1, wherein the mineral acid is selected from sulfuric acid, hydrochloric acid, perchloric acid, nitric acid, phosphoric acid.

7. A method according to claim 6, wherein the mineral acid is at a concentration of less than 5 wt %.

8. A method according to claim 1, wherein the ratio of alkaline earth metal oxide to mineral acid is from 1.5-2.5 to 0.5-1.5.

9. A method according to claim 1, wherein the Lewis acid is a tin halide.

10. A method according to claim 1, wherein the Lewis acid is at a concentration of less than 0.2 to 1.5 wt %.

11. A method according to claim 1, wherein said first mixture of step (b) is dried in vacuo at a temperature of from 40° to 140° C. prior to conducting step (c).

12. A method according to claim 1, wherein step (c) is conducted at a pressure of 0.1 to 10 bar.

13. A method according to claim 1, wherein the alkoxylated fatty acid alkyl ester is isolated by filtration.

14. A method according to claim 1, wherein the second mixture is acidified for neutralization prior to conducting step (d).

15. A method according to claim 1, wherein step (c) is conducted at a pressure of 0.1 to 10 bar and at a temperature of from 40° C. to 200° C.

16. A method according to claim 1, wherein step (c) is conducted at a pressure of 0.1 to 2.0 bar and at a temperature of from 40° C. to 200° C.

17. The method according to claim 1, wherein the ratio of alkaline earth metal oxide to mineral acid is about 2 to 1.

18. The method according to claim 2, wherein R$_3$ and R$_4$ are independently of each other H, methyl or ethyl.

19. The method according to claim 4, wherein the alkaline earth metal oxide is barium oxide.

20. The method according to claim 5, wherein the alkaline earth metal oxide is at a concentration of 0.5 to 1.5 wt %.

21. The method according to claim 19, wherein the alkaline earth metal oxide is at a concentration of 0.5 to 1.5 wt %.

22. A method according to claim 6, wherein the mineral acid is sulfuric acid.

23. The method according to claim 7, wherein the mineral acid is at a concentration of less than 2 wt %.

24. The method according to claim 22, wherein the mineral acid is at a concentration of less than 2 wt %.

* * * * *